(12) United States Patent
Stahmann et al.

(10) Patent No.: US 8,391,974 B2
(45) Date of Patent: *Mar. 5, 2013

(54) APPARATUS AND METHOD FOR PACING MODE SWITCHING DURING ATRIAL TACHYARRHYTHMIAS

(75) Inventors: Jeffrey E. Stahmann, Ramsey, MN (US); Andrew P. Kramer, Marine on St. Croix, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 74 days.

This patent is subject to a terminal disclaimer.

(21) Appl. No.: 12/973,059

(22) Filed: Dec. 20, 2010

(65) Prior Publication Data

US 2011/0087303 A1 Apr. 14, 2011

Related U.S. Application Data

(63) Continuation of application No. 11/733,332, filed on Apr. 10, 2007, now Pat. No. 7,856,267, which is a continuation of application No. 10/713,556, filed on Nov. 13, 2003, now Pat. No. 7,212,860, which is a continuation-in-part of application No. 09/748,796, filed on Dec. 26, 2000, now Pat. No. 7,142,918, and a continuation-in-part of application No. 09/316,515, filed on May 21, 1999, now Pat. No. 7,062,325.

(51) Int. Cl.
*A61N 1/36* (2006.01)

(52) U.S. Cl. ...................................................... 607/14

(58) Field of Classification Search ................ 607/14; 600/518
See application file for complete search history.

(56) References Cited

U.S. PATENT DOCUMENTS

| | | | |
|---|---|---|---|
| 3,857,399 | A | 12/1974 | Zacouto |
| 4,030,510 | A | 6/1977 | Bowers |
| 4,059,116 | A | 11/1977 | Adams |
| 4,163,451 | A | 8/1979 | Lesnick et al. |
| 4,208,008 | A | 6/1980 | Smith |
| RE30,387 | E | 8/1980 | Denniston, III et al. |
| 4,432,360 | A | 2/1984 | Mumford et al. |
| 4,485,818 | A | 12/1984 | Leckrone et al. |
| 4,503,857 | A | 3/1985 | Boute et al. |
| 4,556,063 | A | 12/1985 | Thompson et al. |
| 4,562,841 | A | 1/1986 | Brockway et al. |
| 4,596,255 | A | 6/1986 | Snell et al. |
| 4,791,936 | A | 12/1988 | Snell et al. |
| 4,809,697 | A | 3/1989 | Causey, III et al. |
| 4,830,006 | A | 5/1989 | Haluska et al. |
| 4,856,523 | A | 8/1989 | Sholder et al. |
| 4,860,749 | A | 8/1989 | Lehmann |
| 4,869,252 | A | 9/1989 | Gilli |
| 4,890,617 | A | 1/1990 | Markowitz et al. |

(Continued)

FOREIGN PATENT DOCUMENTS

| | | |
|---|---|---|
| EP | 0033418 A1 | 8/1981 |
| EP | 0360412 A1 | 3/1990 |

(Continued)

OTHER PUBLICATIONS

Metrix™ Model 3020 Implantable Atrial Defibrillator, *Physician's Manual*, InControl, Inc., Redmond, WA, (1998), pp. 4-24-4-27.

(Continued)

*Primary Examiner* — Eric D. Bertram
(74) *Attorney, Agent, or Firm* — Schwegman Lundberg & Woessner, P.A.

(57) ABSTRACT

A method for operating a cardiac pacemaker in which the mode of operation of the pacemaker is altered in response to detecting an episode of atrial tachycardia. In accordance with the invention, the pacemaker's pacing mode is altered in a manner that attempts to maintain hemodynamic stability during the atrial tachycardia. Such a mode switch is particularly applicable to pacemaker patients suffering from some degree of congestive heart failure.

12 Claims, 3 Drawing Sheets

U.S. PATENT DOCUMENTS

| | | |
|---|---|---|
| 4,905,697 A | 3/1990 | Heggs et al. |
| 4,917,115 A | 4/1990 | Flammang et al. |
| 4,920,965 A | 5/1990 | Funke et al. |
| 4,928,688 A * | 5/1990 | Mower ................ 607/9 |
| 4,932,406 A | 6/1990 | Berkovits |
| 4,940,054 A | 7/1990 | Grevis et al. |
| 4,941,471 A | 7/1990 | Mehra |
| 4,944,298 A | 7/1990 | Sholder |
| 4,944,928 A | 7/1990 | Grill et al. |
| 4,945,909 A | 8/1990 | Fearnot et al. |
| 4,972,834 A | 11/1990 | Begemann et al. |
| 4,998,974 A | 3/1991 | Aker |
| 5,012,814 A | 5/1991 | Mills et al. |
| 5,042,480 A | 8/1991 | Hedin et al. |
| 5,077,667 A | 12/1991 | Brown et al. |
| 5,085,215 A | 2/1992 | Nappholz et al. |
| 5,101,824 A | 4/1992 | Lekholm |
| 5,107,850 A | 4/1992 | Olive |
| 5,127,404 A | 7/1992 | Wyborny et al. |
| 5,129,394 A | 7/1992 | Mehra |
| 5,133,350 A | 7/1992 | Duffin |
| 5,139,020 A | 8/1992 | Koestner et al. |
| 5,144,949 A | 9/1992 | Olson |
| 5,156,147 A | 10/1992 | Warren et al. |
| 5,156,154 A | 10/1992 | Valenta, Jr. et al. |
| 5,179,949 A | 1/1993 | Chirife |
| 5,183,040 A | 2/1993 | Nappholz et al. |
| 5,184,614 A | 2/1993 | Collins et al. |
| 5,188,106 A | 2/1993 | Nappholz et al. |
| 5,193,535 A | 3/1993 | Bardy et al. |
| 5,193,550 A | 3/1993 | Duffin |
| 5,197,467 A | 3/1993 | Steinhaus et al. |
| 5,207,219 A | 5/1993 | Adams et al. |
| 5,226,415 A | 7/1993 | Girodo et al. |
| 5,282,836 A | 2/1994 | Kreyenhagen et al. |
| 5,284,491 A | 2/1994 | Sutton et al. |
| 5,292,339 A | 3/1994 | Stephens et al. |
| 5,292,341 A | 3/1994 | Snell |
| 5,311,874 A | 5/1994 | Baumann et al. |
| 5,312,452 A | 5/1994 | Salo |
| 5,331,966 A | 7/1994 | Bennett et al. |
| 5,334,220 A | 8/1994 | Sholder |
| 5,350,409 A | 9/1994 | Stoop et al. |
| 5,356,425 A | 10/1994 | Bardy et al. |
| 5,360,437 A | 11/1994 | Thompson |
| 5,365,932 A | 11/1994 | Greenhut |
| 5,372,607 A | 12/1994 | Stone et al. |
| 5,379,776 A | 1/1995 | Murphy et al. |
| 5,383,910 A | 1/1995 | den Dulk |
| 5,387,229 A | 2/1995 | Poore |
| 5,391,189 A | 2/1995 | van Krieken et al. |
| 5,395,373 A | 3/1995 | Ayers |
| 5,395,397 A | 3/1995 | Lindgren et al. |
| 5,400,796 A | 3/1995 | Wecke |
| 5,411,524 A | 5/1995 | Rahul |
| 5,411,531 A | 5/1995 | Hill et al. |
| 5,417,714 A | 5/1995 | Levine et al. |
| 5,423,869 A | 6/1995 | Poore et al. |
| 5,431,691 A | 7/1995 | Snell et al. |
| 5,437,285 A | 8/1995 | Verrier et al. |
| 5,462,060 A | 10/1995 | Jacobson et al. |
| 5,474,574 A | 12/1995 | Payne et al. |
| 5,480,413 A | 1/1996 | Greenhut et al. |
| 5,486,198 A | 1/1996 | Ayers et al. |
| 5,487,752 A | 1/1996 | Salo et al. |
| 5,507,782 A | 4/1996 | Kieval et al. |
| 5,507,784 A | 4/1996 | Hill et al. |
| 5,514,163 A | 5/1996 | Markowitz et al. |
| 5,522,850 A | 6/1996 | Yomtov et al. |
| 5,522,859 A | 6/1996 | Stroebel et al. |
| 5,523,942 A | 6/1996 | Tyler et al. |
| 5,527,347 A | 6/1996 | Shelton et al. |
| 5,534,016 A | 7/1996 | Boute |
| 5,540,232 A | 7/1996 | Laney et al. |
| 5,540,727 A | 7/1996 | Tockman et al. |
| 5,545,182 A | 8/1996 | Stotts et al. |
| 5,545,186 A | 8/1996 | Olson et al. |
| 5,549,649 A | 8/1996 | Florio et al. |
| 5,549,654 A | 8/1996 | Powell |
| 5,554,174 A | 9/1996 | Causey, III |
| 5,560,369 A | 10/1996 | McClure et al. |
| 5,560,370 A | 10/1996 | Verrier et al. |
| 5,584,864 A | 12/1996 | White |
| 5,584,867 A | 12/1996 | Limousin et al. |
| 5,591,215 A | 1/1997 | Greenhut et al. |
| 5,605,159 A | 2/1997 | Smith et al. |
| 5,607,460 A | 3/1997 | Kroll et al. |
| 5,613,495 A | 3/1997 | Mills et al. |
| 5,620,471 A | 4/1997 | Duncan |
| 5,620,473 A | 4/1997 | Poore |
| 5,622,178 A | 4/1997 | Gilham |
| 5,626,620 A | 5/1997 | Kieval et al. |
| 5,626,622 A | 5/1997 | Cooper |
| 5,626,623 A | 5/1997 | Kieval et al. |
| 5,632,267 A | 5/1997 | Hognelid et al. |
| 5,674,250 A | 10/1997 | de Coriolis et al. |
| 5,674,251 A | 10/1997 | Combs et al. |
| 5,674,255 A | 10/1997 | Walmsley et al. |
| 5,676,153 A | 10/1997 | Smith et al. |
| 5,683,429 A | 11/1997 | Mehra |
| 5,690,686 A | 11/1997 | Min et al. |
| 5,690,689 A | 11/1997 | Sholder |
| 5,700,283 A | 12/1997 | Salo |
| 5,702,424 A | 12/1997 | Legay et al. |
| 5,713,928 A | 2/1998 | Bonnet et al. |
| 5,713,929 A | 2/1998 | Hess et al. |
| 5,713,930 A | 2/1998 | van der Veen et al. |
| 5,713,932 A | 2/1998 | Gillberg et al. |
| 5,716,382 A | 2/1998 | Snell |
| 5,716,383 A | 2/1998 | Kieval et al. |
| 5,716,384 A | 2/1998 | Snell |
| 5,718,235 A | 2/1998 | Golosarsky et al. |
| 5,724,985 A | 3/1998 | Snell et al. |
| 5,725,559 A | 3/1998 | Alt et al. |
| 5,725,561 A | 3/1998 | Stroebel et al. |
| 5,730,141 A | 3/1998 | Fain et al. |
| 5,730,142 A | 3/1998 | Sun et al. |
| 5,738,096 A | 4/1998 | Ben-Haim |
| 5,741,304 A | 4/1998 | Patwardhan et al. |
| 5,741,308 A | 4/1998 | Sholder |
| 5,749,901 A | 5/1998 | Bush et al. |
| 5,749,906 A | 5/1998 | Kieval et al. |
| 5,755,736 A | 5/1998 | Gillberg et al. |
| 5,755,737 A | 5/1998 | Prieve et al. |
| 5,755,739 A | 5/1998 | Sun et al. |
| 5,755,740 A | 5/1998 | Nappholz |
| 5,759,196 A | 6/1998 | Hess et al. |
| 5,776,164 A | 7/1998 | Ripart |
| 5,776,167 A | 7/1998 | Levine et al. |
| 5,782,887 A | 7/1998 | van Krieken et al. |
| 5,782,888 A | 7/1998 | Sun et al. |
| 5,788,717 A | 8/1998 | Mann et al. |
| 5,792,193 A | 8/1998 | Stoop |
| 5,792,200 A | 8/1998 | Brewer |
| 5,800,464 A | 9/1998 | Kieval |
| 5,800,471 A | 9/1998 | Baumann |
| 5,814,077 A | 9/1998 | Sholder et al. |
| 5,814,081 A | 9/1998 | Ayers et al. |
| 5,814,085 A | 9/1998 | Hill |
| 5,836,975 A | 11/1998 | DeGroot |
| 5,836,987 A | 11/1998 | Baumann et al. |
| 5,840,079 A | 11/1998 | Warman et al. |
| 5,842,997 A | 12/1998 | Verrier et al. |
| 5,846,263 A | 12/1998 | Peterson et al. |
| 5,853,426 A | 12/1998 | Shieh |
| 5,855,593 A | 1/1999 | Olson et al. |
| 5,861,007 A | 1/1999 | Hess et al. |
| 5,865,838 A | 2/1999 | Obel et al. |
| 5,871,507 A | 2/1999 | Obel et al. |
| 5,873,895 A | 2/1999 | Sholder et al. |
| 5,873,897 A | 2/1999 | Armstrong et al. |
| 5,876,422 A | 3/1999 | van Groeningen |
| 5,891,178 A | 4/1999 | Mann et al. |
| 5,893,882 A * | 4/1999 | Peterson et al. ................ 607/14 |
| 5,897,575 A | 4/1999 | Wickham |
| 5,902,324 A | 5/1999 | Thompson et al. |
| 5,928,271 A | 7/1999 | Hess et al. |

| | | |
|---|---|---|
| 5,931,856 A | 8/1999 | Bouhour et al. |
| 5,931,857 A | 8/1999 | Prieve et al. |
| 5,935,081 A | 8/1999 | Kadhiresan |
| 5,944,744 A | 8/1999 | Paul et al. |
| 5,951,592 A | 9/1999 | Murphy |
| 5,968,079 A | 10/1999 | Warman et al. |
| 5,968,081 A | 10/1999 | Levine |
| 5,974,341 A | 10/1999 | Er et al. |
| 5,978,707 A | 11/1999 | Krig et al. |
| 5,978,710 A | 11/1999 | Prutchi et al. |
| 5,983,138 A | 11/1999 | Kramer |
| 5,987,354 A | 11/1999 | Cooper et al. |
| 5,987,356 A | 11/1999 | DeGroot |
| 5,991,656 A | 11/1999 | Olson et al. |
| 5,991,657 A | 11/1999 | Kim |
| 5,991,662 A | 11/1999 | Kim et al. |
| 5,999,850 A | 12/1999 | Dawson et al. |
| 5,999,854 A | 12/1999 | Deno et al. |
| 6,026,320 A | 2/2000 | Carlson et al. |
| 6,041,251 A | 3/2000 | Kim et al. |
| 6,044,298 A | 3/2000 | Salo et al. |
| 6,047,210 A | 4/2000 | Kim et al. |
| 6,049,735 A | 4/2000 | Hartley et al. |
| 6,052,617 A | 4/2000 | Kim |
| 6,052,620 A | 4/2000 | Gillberg et al. |
| 6,058,328 A | 5/2000 | Levine et al. |
| 6,070,101 A | 5/2000 | Struble et al. |
| 6,081,745 A | 6/2000 | Mehra |
| 6,081,746 A | 6/2000 | Pendekanti et al. |
| 6,081,747 A | 6/2000 | Levine et al. |
| 6,081,748 A | 6/2000 | Struble et al. |
| RE36,765 E | 7/2000 | Mehra |
| 6,085,116 A | 7/2000 | Pendekanti et al. |
| 6,088,618 A | 7/2000 | Kerver |
| 6,091,988 A | 7/2000 | Warman et al. |
| 6,096,064 A | 8/2000 | Routh |
| 6,122,545 A | 9/2000 | Struble et al. |
| 6,128,529 A | 10/2000 | Esler |
| 6,129,745 A | 10/2000 | Sun et al. |
| 6,134,469 A | 10/2000 | Wietholt |
| 6,151,524 A | 11/2000 | Krig et al. |
| 6,219,579 B1 | 4/2001 | Bakels et al. |
| 6,223,072 B1 | 4/2001 | Mika et al. |
| 6,223,079 B1 | 4/2001 | Bakels et al. |
| 6,223,082 B1 | 4/2001 | Bakels et al. |
| 6,238,420 B1 | 5/2001 | Bakels et al. |
| 6,246,909 B1 | 6/2001 | Ekwall |
| 6,249,699 B1 | 6/2001 | Kim |
| 6,256,534 B1 | 7/2001 | Dahl |
| 6,263,242 B1 | 7/2001 | Mika et al. |
| 6,266,554 B1 | 7/2001 | Hsu et al. |
| 6,272,380 B1 | 8/2001 | Warman et al. |
| 6,275,734 B1 | 8/2001 | McClure et al. |
| 6,280,391 B1 | 8/2001 | Olson et al. |
| 6,285,907 B1 | 9/2001 | Kramer et al. |
| 6,292,693 B1 | 9/2001 | Darvish et al. |
| 6,317,632 B1 | 11/2001 | Krig et al. |
| 6,351,669 B1 | 2/2002 | Hartley et al. |
| 6,353,759 B1 | 3/2002 | Hartley et al. |
| 6,353,761 B1 | 3/2002 | Conley et al. |
| 6,408,209 B1 | 6/2002 | Bouhour et al. |
| 6,411,847 B1 | 6/2002 | Mower |
| 6,411,848 B2 | 6/2002 | Kramer et al. |
| 6,424,865 B1 | 7/2002 | Ding |
| 6,430,438 B1 | 8/2002 | Chen et al. |
| 6,434,424 B1 | 8/2002 | Igel et al. |
| 6,438,410 B2 | 8/2002 | Hsu et al. |
| 6,501,987 B1 | 12/2002 | Lovett et al. |
| 6,501,988 B2 | 12/2002 | Kramer et al. |
| 6,512,951 B1 | 1/2003 | Marcovecchio et al. |
| 6,522,925 B1 | 2/2003 | Gilkerson et al. |
| RE38,119 E | 5/2003 | Mower |
| 6,687,541 B2 | 2/2004 | Marcovecchio et al. |
| 6,763,267 B2 | 7/2004 | Ding |
| 6,847,842 B1 | 1/2005 | Rodenhiser et al. |
| 6,957,100 B2 | 10/2005 | Vanderlinde et al. |
| 6,988,002 B2 | 1/2006 | Kramer et al. |
| 7,039,461 B1 | 5/2006 | Lovett |
| 7,047,066 B2 | 5/2006 | Vanderlinde et al. |
| 7,062,325 B1 | 6/2006 | Krig et al. |
| 7,069,077 B2 | 6/2006 | Lovett et al. |
| 7,120,490 B2 | 10/2006 | Chen et al. |
| 7,142,915 B2 | 11/2006 | Kramer et al. |
| 7,142,918 B2 | 11/2006 | Stahmann et al. |
| 7,181,278 B2 | 2/2007 | Kramer et al. |
| 7,212,860 B2 | 5/2007 | Stahmann et al. |
| 7,239,914 B2 | 7/2007 | Lovett et al. |
| 7,383,086 B2 | 6/2008 | Ding |
| 7,460,908 B2 | 12/2008 | Krig et al. |
| 7,680,530 B2 | 3/2010 | Vanderlinde et al. |
| 7,742,814 B2 | 6/2010 | Lovett |
| 7,805,192 B2 | 9/2010 | Stahmann et al. |
| 7,856,267 B2 | 12/2010 | Stahmann et al. |
| 7,996,086 B2 | 8/2011 | Stahmann et al. |
| 2002/0062139 A1 | 5/2002 | Ding |
| 2002/0082509 A1 | 6/2002 | Vanderlinde et al. |
| 2002/0082660 A1 | 6/2002 | Stahmann et al. |
| 2002/0087198 A1 | 7/2002 | Kramer et al. |
| 2002/0091415 A1 | 7/2002 | Lovett et al. |
| 2002/0120298 A1 | 8/2002 | Kramer et al. |
| 2003/0004551 A1 | 1/2003 | Chen et al. |
| 2003/0069610 A1 | 4/2003 | Kramer et al. |
| 2003/0078630 A1 | 4/2003 | Lovett et al. |
| 2003/0105491 A1 | 6/2003 | Gilkerson et al. |
| 2003/0233131 A1 | 12/2003 | Kramer et al. |
| 2004/0010295 A1 | 1/2004 | Kramer et al. |
| 2004/0215249 A1 | 10/2004 | Corbucci |
| 2004/0215259 A1 | 10/2004 | Krig et al. |
| 2004/0243188 A1 | 12/2004 | Vanderlinde et al. |
| 2005/0038480 A1 | 2/2005 | Ding |
| 2007/0016258 A1 | 1/2007 | Krig et al. |
| 2007/0135853 A1 | 6/2007 | Kramer et al. |
| 2007/0233201 A1 | 10/2007 | Lovett et al. |
| 2007/0288062 A1 | 12/2007 | Stahmann et al. |
| 2009/0076563 A1 | 3/2009 | Krig et al. |
| 2010/0145407 A1 | 6/2010 | Vanderlinde et al. |
| 2010/0249866 A1 | 9/2010 | Lovett |

FOREIGN PATENT DOCUMENTS

| | | |
|---|---|---|
| EP | 0401962 A2 | 12/1990 |
| EP | 0597459 A2 | 5/1994 |
| EP | 0617980 A2 | 10/1994 |
| EP | 0748638 A2 | 12/1996 |
| WO | WO-93/02746 A1 | 2/1993 |
| WO | WO-95/09029 A2 | 4/1995 |
| WO | WO-97/11745 A1 | 4/1997 |
| WO | WO-97/39798 A1 | 10/1997 |
| WO | WO-98/48891 A1 | 11/1998 |
| WO | WO-00/04950 A2 | 2/2000 |
| WO | WO-00/38782 A1 | 7/2000 |
| WO | WO-00/71200 A1 | 11/2000 |
| WO | WO-00/71202 A1 | 11/2000 |
| WO | WO-00/71203 A1 | 11/2000 |

OTHER PUBLICATIONS

"U.S. Appl. No. 10/713,556, Non Final office action mailed Jun. 12, 2006", 22 pgs.

"U.S. Appl. No. 10/713,556, Notice of Allowance mailed Dec. 18, 2006", 9 pgs.

"U.S. Appl. No. 10/713,556, Response filed Oct. 12, 2006 to Non Final Office Action mailed Jun. 12, 2006", 9 pgs.

"U.S. Appl. No. 11/733,332, Advisory Action mailed Oct. 27, 2009", 3 pgs.

"U.S. Appl. No. 11/733,332, Final Office Action mailed Aug. 3, 2009", 9 pgs.

"U.S. Appl. No. 11/733,332, Non-Final Office Action mailed Feb. 17, 2009", 8 pgs.

"U.S. Appl. No. 11/733,332, Notice of Allowance mailed Jul. 14, 2010", 7 pgs.

"U.S. Appl. No. 11/733,332, Response filed May 18, 2009 to Non-Final Office Action mailed Feb. 17, 2009", 8 pgs.

"U.S. Appl. No. 11/733,332, Response filed Oct. 5, 2009 to Final Office Action mailed Aug. 3, 2009", 7 pgs.

"French CNH Equipment Approvals", Clinica, 417, p. 9, (Sep. 5, 1990), 3 pgs.

"Harmony™, Automatic Dual Chamber Pacemaker, Product Information and Programming Guide", Viatron Medical, 22 p., (Published Prior to Nov. 13, 2003), Harmony Dual Chamber mentioned in publication *Clinica*, 467, p. 16, Sep. 11, 1991, "Rate Devices Impact Pacemaker Market", also mentioned in *Clinica*, 417, p. 9, Sep. 5, 1990 French CNH Equi, 22 p.

"Pacemaker System Guide for PULSAR MAX II; Mulitprogrammable Pacemakers", *Product brochure published by Guidant Corporation*, (Apr. 18, 1999), pp. 6-48 and 6-49.

"Pacemaker System Guide for PULSAR MAX II; Multiprogrammable Pacemakers", *Product brochure published by Guidant Corporation*, (Apr. 18, 1999), p. 6-39-6-51.

"Rate-Adaptive Devices Impace Pacemaker Market", *Clinica*, 467, p. 16, (Sep. 11, 1991), 6 pgs.

Ayers, Gregory M., et al.; "Ventricular Proarrhythmic Effects of Ventricular Cycle Length and Shock Strength in a Sheep Model of Transvenous Atrial Defibrillation", *Circulation*, 89 (1), (Jan. 1994), 413-422.

Blommaert, D., et al., "Effective Prevention of Atrial Fibrillation by Continuous Atrial Overdrive Pacing After Coronary Artery Bypass Surgery", *JACC*, vol. 35, No. 6, (May 2000), pp. 1411-1415.

Buhr, T. A., et al., "Novel Pacemaker Algorithm Diminishes Short-Coupled Ventricular Beats in Atrial Fibrillation", *Pacing and Clinical Electrophysiology*, vol. 24, Part II, (Abstract Only), (Apr. 2001), p. 729.

Campbell, R. M., et al., "Atrial Overdrive Pacing for Conversion of Atrial Flutter in Children", *Pediatrics*, 75(4), (Apr. 1985), 730-736.

Clark, David M., et al., "Hemodynamic Effects of an Irregular Sequence of Ventricular Cycle Lengths During Atrial Fibrillation", *JACC*, vol. 30, No. 4, (Oct. 1997), 1039-1045.

Duckers, H. J., et al., "Effective use of a novel rate-smoothing algorithm in atrial fibrillation by ventricular pacing", *European Heart Journal*. 18, (1997), 1951-1955.

Fahy, G. J., et al., "Pacing Strategies to Prevent Atrial Fibrillation", *Atrial Fibrillation*, 14(4), (Nov. 1996), 591-596.

Fromer, M., et al., "Algorithm for the Prevention of Ventricular Tachycardia Onset: The Prevent Study", *The American Journal of Cardiology*, 83 (5B), (Mar. 11, 1999), pp. 45D-47D.

Garrigue, S., et al., "Prevention of Atrial Arrhythmias during DDD Pacing by Atrial Overdrive", *Pacing and Clinical Electrophysiology*, 21(9), (Sep. 1998), 1751-1759.

Greenhut, S., et al., "Effectiveness of a Ventricular Rate Stabilization Algorithm During Atrial Fibrillation in Dogs", *Pace Abstract*, Abstract No. 60, (1996), 1 pg.

Guidant, "CONTAK CD® CRT-D 1823", Physician's System Manual, Cardiac Resynchronization Therapy Defibrillator, (2002), 1-176.

Guidant, "CONTAK® Renewal™ Model H135", System Guide, (2003), 1-331.

Guidant, "CONTAK TR™ CHFD™ Model 1241", *System Guide*, Congestive Heart Failure Device, (1999), 1-191.

Heuer, H., et al., "Dynamic Dual-Chamber Overdrive Pacing with an Implantable Pacemaker System: A New Method for Terminating Slow Ventricular Tachycardia", Zeitschrift fur Kardiologie, 75, German Tranaslation by the Ralph McElroy Translation Company, Austin, TX, (1986), 6 pages.

Heuer, H., et al., "Dynamische Zweikammer-Overdrive-Stimulation mit einem implantierbaren Schrittmachersystem als neue Methode zur Beendigung Langsamer ventrikularer Tachykardien", *Z Kardiol;* 75, Includes English translation (5 pgs.), (1986), pp. 673-675.

Jenkins, J., et al., "Diagnosis of Atrial Fibrillation Using Electrogram from Chronic Leads: Evaluation of Computer Algorithm", *Pacing and Clinical Electrophysiology*, 11(5), (1988), 622-631.

Jung, J., et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998), pp. 689-695.

Krig, D. B, et al., "Method and Apparatus for Treating Irregular Ventricular Contractions Such As During Atrial Arrhythmia", U.S. Appl. No. 09/316,515, filed May 21, 1999, 57 pgs.

Krig, D. B., et al, "Method and Apparatus for Treating Irregular Ventricular Contractions Such as During Atrial Arrhythmia", U.S. Appl. No. 10/643,590, filed Aug. 19, 2003, 45 pgs.

Lau, Chu-Pak, et al., "Efficacy of Ventricular Rate Stabilization by Right Ventricular Pacing During Atrial Fibrillation", *Pacing and Clinical Electrophysiology*, 21(3), (Mar. 1998), 542-548.

Lovett, E. G., "Cardiac Pacing System for Prevention of Ventricular Fibrillation and Ventricular Tachycardia Episodes", U.S. Appl. No. 09/569,295, filed May 13, 2000, 30 pgs.

Marcovecchio, A. F., et al., "Method for Delivering Atrial Defibbillation Therapy", U.S. Appl. No. 10/734,737, filed Nov. 12, 2003, 16 pgs.

Medtronic, "INSYNC® Device Model 8040", *Device Reference Guide*, (Aug. 2001), 1-276.

Medtronic, "INSYNC® ICD 7272", System Reference Guide, Dual chamber implantable cardioverter defibrillator with cardiac resynchronization therapy, A guide to the operation and programming of the 7272 InSync ICD Dual Chamber ImpLantable Cardioverter Defibrillator, (Jun. 2002), 1-367.

Medtronic, "INSYNC® III Device Model 8042", *Device Programming Guide. INSYNC® III Device Model 8042*, Vision Programmer Software Model 9981, (2000), 1-260.

Medtronic, "INSYNC® III Device Model 8042", *Device Reference Guide, INSYNC® III Device Model 8042*, Vision Programmer Software Model 9981, (2002), 1-252.

Medtronic, "INSYNC Marquis™ 7277", *Reference Manual*, Dual Chamber Impiantable Cardioverter Defibrillator, (Mar. 2003), 1-435.

Medtroni, "INSYNC® Model 8040 Device Programming Guide", Device Programming Guide, Device Model 8040 & Programmer Software Model 9980, (2001), 1-204.

Mehra, R., et al., "Prevention of Atrial Fibrillation/Flutter by Pacing Techniques", *Interventional Electrophysiology*, Second Edition, Chapter 34, Futura Publishing Company, Inc., (1986), pp. 521-540.

Morris, M. M., et al., "Intracardiac Electrogram Transformation: Morphometric Implications for Implantable Devices", *Journal of Electrocardiology, 29 Supplement*, (1996), 124-129.

Mower, Morton, U.S. Patent Office Patent Application Information Retrieval search results for U.S. Appl. No. 10/214,474, filed Aug. 8, 2002, entitled "Method and Apparatus for Treating Hemodynamic Disfunction", 3 pgs.

Murgatroyd, F. D., et al., "A New Pacing Algorithm for Overdrive Suppression of Atrial Fibrillation", *Pacing and Clinical Electrophysiology*, 17(11 Pt. 2), (Nov. 1994, Part), 1966-1973.

Schuller, H., et al., "Far Field R-Wave Sensing—An Old Problem Repeating", *Pacing and Clinical Electrophysiology*, 19, Part II, NASPE Abstract No. 264, (1996), p. 631.

Seim, G., et al., "Classification of Atrial Flutter and Atrial Fibrillation Using an Atrial Dispersion Index (ADI)", *Guidant CRM Therapy Research Peer Review Report Revision 2.0*, (Jan. 6, 1999), 27 p.

St. Jude Medical, "Atlas™ + HF Models V-343, V-341", *User's Manual*, Implantable Cardioverter-Defibrillator, (Sep. 2003), 1-30.

St. Jude Medical, "Epic™ HF Model V-339", *User's Manual*, Implantable Cardioverter-Defibrillator, (Jul. 2002). 1-26.

St. Jude Medical, "Model 3510 Programmer with Model 3307 Software", Reference Manual, For Atlas™, Atlas™+, Epic™, Epic™+ Photon™ μ and Photon™ Implantable Cardioverter/Defibrillators, (Sep. 2003), 1-314.

Stahmann, J. E., et al., "Apparatus and Method for Pacing Mode Switching During Atrial Tachyarrhythmias", U.S. Appl. No. 09/748,796, filed Dec. 26, 2000, 44 pgs.

Stephany, G. R., et al., "Real-Time Estimation of Magnitude-Square Coherence for Use in Implantable Devices", *IEEE Computers in Cardiology*, (1992), 375-378.

Sutton, R., "Pacing in Atrial Arrhythmias", *Pacing and Clinical Electrophysiology*, 13(12), (Dec. 1990, Part), 1823-1827.

Swiryn, S., et al., "Detection of Atrial Fibrillation by Pacemakers and Antiarrhythmic Devices", *Nonpharmacological Management of Atrial Fibrillation*, Chapter 21, Futura Publishing Co, Inc. Armonk, NY, (1997), 309-318.

Wittkampf, F. H. M., et al., "Rate Stabilization by Right Ventricular Pacing in Patients with Atrial Fibrillation", *Pacing and Clinical Electrophysiology*, 9(6, Part 2), (Nov.-Dec. 1986), 1147-1153.

Wittkampf, F. H.M., et al., "Effect of Right Ventricular Pacing on Ventricular Rhythm During Atrial Fibrilation", *JACC*, vol. 11, No. 3, (Mar. 1988), 539-545.

Zhu, D. W, "Electrophysiology, Pacing and Arrhythmia—Pacing Therapy for Atrial Tachyarrhythmias", *Clinical Cardiology*, 19(9), (1996), 737-742.

* cited by examiner

APPARATUS AND METHOD FOR PACING MODE SWITCHING DURING ATRIAL TACHYARRHYTHMIAS

CROSS REFERENCE TO RELATED APPLICATION(S)

This application is a continuation of U.S. patent application Ser. No. 11/733,332, filed on Apr. 10, 2007, now issued as U.S. Pat. No. 7,856,267, which is a continuation of U.S. patent application Ser. No. 10/713,556, filed on Nov. 13, 2003, now issued as U.S. Pat. No. 7,212,860, which is a continuation-in-part of the following commonly assigned patent applications: U.S. patent application Ser. No. 09/748,796 filed on Dec. 26, 2000, now issued as U.S. Pat. No. 7,142,918, and U.S. patent application Ser. No. 09/316,515 filed on May 21, 1999, now issued as U.S. Pat. No. 7,062,325, the specifications of which are herein incorporated by reference in their entirety. This application also incorporates by reference in its entirety U.S. patent application Ser. No. 09/316,588 which issued as U.S. Pat. No. 6,285,907.

FIELD OF THE INVENTION

This invention pertains to cardiac pacemakers and methods for operating such devices. In particular, the invention relates to methods for cardiac pacing during an atrial tachyarrhythmia.

BACKGROUND

Congestive heart failure (CHF) is a clinical syndrome in which an abnormality of cardiac function causes cardiac output to fall below a level adequate to meet the metabolic demand of peripheral tissues. CHF can be due to a variety of etiologies with that due to ischemic heart disease being the most common. Some form of cardiac pacing can often benefit CHF patients. For example, sinus node dysfunction resulting in bradycardia can contribute to heart failure which can be corrected with conventional bradycardia pacing. Also, some CHF patients suffer from some degree of AV block such that their cardiac output is improved by synchronizing atrial and ventricular contractions with dual-chamber pacing using a programmed AV delay time (i.e., atrial triggered ventricular pacing or AV sequential pacing).

A common sequela of CHF is dilation of the heart chambers (especially the left ventricle) as end-diastolic volume is increased in the body's attempt to increase stroke volume. The ventricles can then become stretched and less contractile which actually worsens the heart failure. Stretching of the ventricular wall can also cause slowed conduction of depolarization impulses through the ventricle. If conduction velocity is slowed in the left ventricle more than the right, for example, the contraction of the two ventricles during ventricular systole becomes uncoordinated which lessens pumping efficiency. Some CHF patients also suffer from conduction defects of the specialized conduction system of the heart (a.k.a. bundle branch blocks) so that a depolarization impulse from the AV node reaches one ventricle before the other. In both of these situations, cardiac output can be increased by improving the synchronization of right and left ventricular contractions. Cardiac pacemakers have therefore been developed which provide pacing to both ventricles. (See, e.g., U.S. Pat. No. 4,928,688, issued to Mower and hereby incorporated by reference.)

Due to stretching of the atrial walls caused by the cardiac dilation described above, CHF patients are predisposed to occurrence of atrial tachyarrhythmias. Atrial tachyarrhythmias are cardiac rhythms characterized by atrial contractions occurring at a rapid rate, either due to an ectopic excitatory focus or abnormal excitation by normal pacemaker tissue. Atrial tachyarrhythmias can be classified according to increasing rate into entities that include atrial tachycardia, atrial flutter, and atrial fibrillation. Due to the refractory period of the AV node, some degree of AV block is usually always present so that the ventricular rate is less than the atrial rate if the AV conduction pathway is otherwise intact. In atrial fibrillation, the atria depolarize in a chaotic fashion with no effective pumping action, and the ventricles beat both rapidly and irregularly due to conduction of excitatory impulses from the fibrillating atria through the AV node. In atrial tachyarrhythmias, and especially atrial fibrillation, the atria no longer act as effective primer pumps for the ventricles which decreases stroke volume, referred to as a loss of atrio-ventricular synchrony. Also, when the ventricles contract at irregular intervals, the contraction can occur prematurely before diastolic filling is complete and decrease the stroke volume for that contraction. An episode of atrial tachyarrhythmia can thus depress cardiac output and cause such symptoms as dyspnea, fatigue, vertigo, and angina. This is especially problematic in CHF patients who are already hemodynamically compromised.

SUMMARY OF THE INVENTION

The present invention relates to a method and system for altering the pacing mode of a pacemaker in order to maintain hemodynamic stability during an atrial tachyarrhythmia such as atrial fibrillation. The invention may be especially beneficial to pacemaker patients with CHF whose hemodynamics are adversely affected by episodes of atrial fibrillation.

In accordance with the invention, the pacing mode of a pacemaker is switched from a normal pacing mode to an atrial fibrillation pacing mode in response to detection of an atrial tachyarrhythmia. The atrial fibrillation pacing mode is adapted for pacing in the presence of an irregular intrinsic ventricular rhythm. Depending upon the individual patient and the normal pacing mode, the atrial fibrillation mode may include initiation or modification of ventricular resynchronization therapy, initiation of ventricular rate regularization pacing, and/or changes to rate-adaptive parameters.

In one embodiment, the atrial fibrillation mode includes ventricular resynchronization, wherein pacing stimulation is applied to both ventricles or to one ventricle in a manner that improves the coordination of ventricular contractions. Such pacing is beneficial in patients with interventricular or intraventricular conduction defects, and switching to a resynchronization mode during an episode of atrial tachyarrhythmia improves cardiac output in those patients. If the normal pacing mode already includes resynchronization therapy, it may be beneficial to modify the resynchronization in the atrial fibrillation mode by, for example, adjusting a biventricular offset value or initiating biventricular triggered pacing.

In another embodiment, the atrial fibrillation mode includes ventricular rate regularization where a ventricular escape interval is dynamically adjusted in accordance with a measured intrinsic ventricular rate. By adjusting the ventricular escape interval to more nearly match the intrinsic ventricular rate, more paces are delivered and less variability in the overall ventricular rhythm is allowed. With a more regular ventricular rate, cardiac output is improved during an atrial tachyarrhythmia. Ventricular rate regularization may also enhance the effectiveness of ventricular resynchronization pacing in the presence of an atrial tachyarrhythmia by increasing the number of paces delivered.

DESCRIPTION OF THE INVENTION

The most common condition for which pacemakers are used is in the treatment of bradycardia, where the ventricular rate is too slow. Atrio-ventricular conduction defects (i.e., AV block) that are fixed or intermittent and sick sinus syndrome represent the most common causes of bradycardia for which permanent pacing may be indicated. If functioning properly, a pacemaker makes up for the heart's inability to pace itself at an appropriate rhythm in order to meet metabolic demand by enforcing a minimum heart rate. As described below, bradycardia pacing modes define which chambers are paced and the manner in which the paces are delivered. Pacing therapy can also be used in the treatment of congestive heart failure (CHF). Some CHF patients suffer from some degree of AV block or are chronotropically deficient such that their cardiac output can be improved with conventional bradycardia pacing. It has also been shown, however, that some CHF patients suffer from intraventricular and/or interventricular conduction defects such that their cardiac outputs can be increased by improving the synchronization of right and left ventricular contractions with electrical stimulation, referred to herein as ventricular resynchronization therapy.

A pacemaker patient with some degree of CHF who experiences an episode of atrial fibrillation will suffer some diminishing of cardiac output from the resulting irregular ventricular rhythm and/or loss of atrio-ventricular synchrony. Thus, even if a patient were adequately treated during normal circumstances with only a bradycardia pacing mode, the same patient may benefit from resynchronization therapy to restore hemodynamic stability during the atrial fibrillation episode. Furthermore, patients treated with resynchronization therapy in addition to a bradycardia pacing mode may benefit from a modification to the pacing mode including changes to the mode of resynchronization. The present invention relates to a method for operating a pacemaker in which a normal pacing mode is switched to an atrial fibrillation pacing mode upon detection of an atrial tachyarrhythmia such as atrial fibrillation that counteracts the adverse effects of atrial fibrillation.

1. Hardware Platform

Cardiac pacemakers are cardiac rhythm management devices that provide electrical stimulation in the form of pacing pulses to selected chambers of the heart. (As the term is used herein, a pacemaker is any cardiac rhythm management device that performs cardiac pacing, including implantable cardioverter/defibrillators having a pacing functionality.) Cardiac rhythm management devices are typically implanted subcutaneously in a patient's chest and have leads threaded intravenously into the heart to connect the device to electrodes used for sensing and pacing, the electrodes being disposed in proximity to selected chambers of the heart. Pacemakers typically have a programmable electronic controller that causes the pacing pulses to be output in response to lapsed time intervals and sensed electrical activity (i.e., intrinsic heart beats not as a result of a pacing pulse). A depolarization wave associated with an intrinsic contraction of the atria or ventricles that is detected by the pacemaker is referred to as an atrial sense (P wave) or ventricular sense (R wave), respectively. In order to cause such a contraction in the absence of an intrinsic beat, a pacing pulse with energy above a certain pacing threshold is delivered to the chamber.

Figure 1:
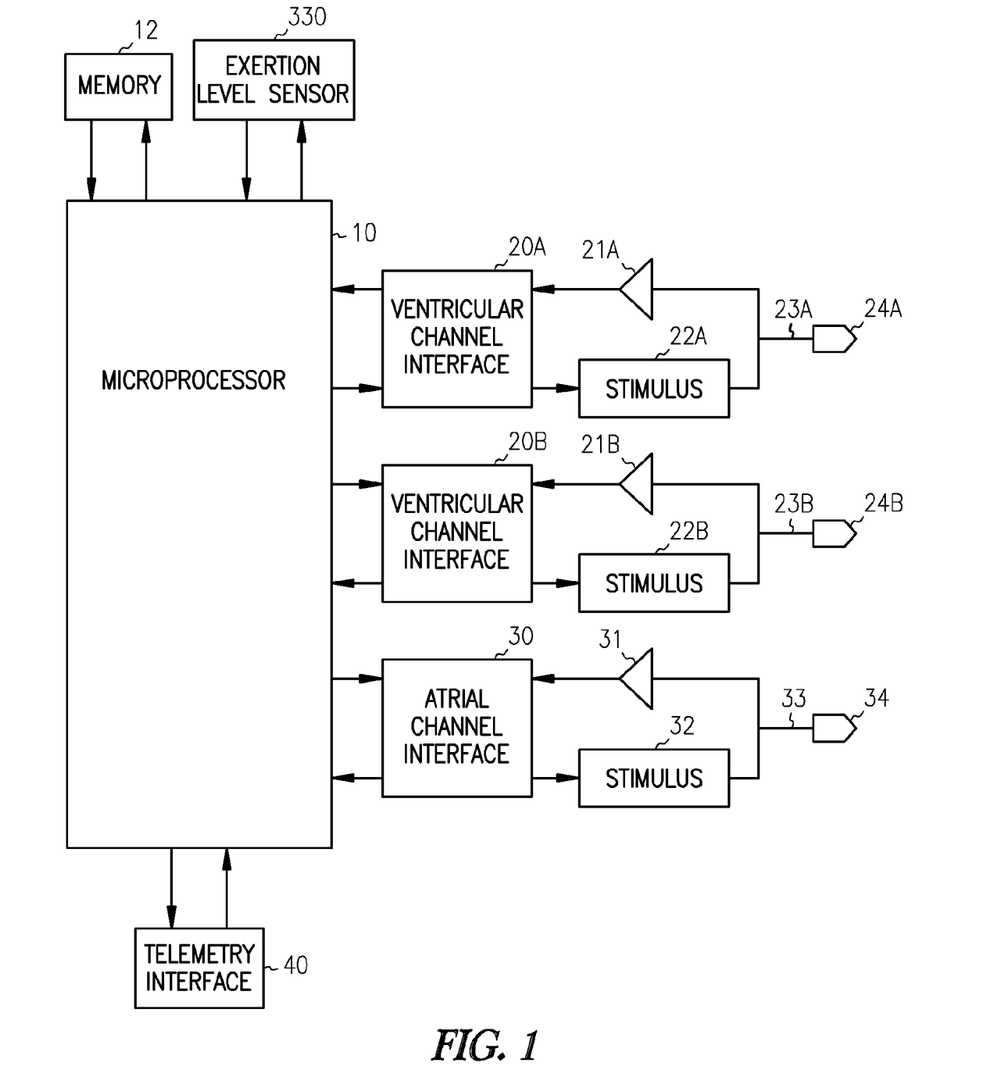
FIG. 1 is a system diagram of a microprocessor-based pacemaker.

FIG. 1 shows a system diagram of a microprocessor-based pacemaker physically configured with sensing and pacing channels for the atrium and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The device also has ventricular sensing and pacing channels for both ventricles comprising electrodes 24A-B, leads 23A-B, sensing amplifiers 21A-B, pulse generators 22A-B, and ventricular channel interfaces 20a-b where "A" designates one ventricular channel and "B" designates the other. For each channel, the same lead and electrode are used for both sensing and pacing. The channel interfaces 20A-B and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels in accordance with a pacing mode, interprets sense signals from the sensing channels, and implements timers for defining escape intervals and sensory refractory periods. The controller also detects the presence of arrhythmias such as atrial fibrillation by measuring the time interval between senses and implements the mode switching function as described herein. It should be appreciated that these functions could also be performed by custom logic circuitry either in addition to or instead of a programmed microprocessor.

2. Bradycardia Pacing Modes

Bradycardia pacing modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-triggered ventricular pacing attempts to maintain the atrio-ventricular synchrony occurring with physiological beats whereby atrial contractions augment diastolic filling of the ventricles. If a patient has a physiologically normal atrial rhythm, atrial-triggered pacing also allows the ventricular pacing rate to be responsive to the metabolic needs of the body. Atrial tracking modes are contraindicated when there is chronic refractory atrial tachyarrhythmia such as atrial fibrillation or atrial flutter.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate interval is then the sum of the atrial escape interval and the atrio-ventricular interval.

Rate-adaptive pacemakers modulate the ventricular and/or atrial escape intervals base upon measurements corresponding to physical activity. Such pacemakers are applicable to situations in which atrial tracking modes cannot be use. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate.

3. Ventricular Resynchronization Therapy

In a ventricular resynchronization pacing mode, pacing stimulation is applied to one or both ventricles in a manner that improves the coordination of ventricular contractions and thereby improves ventricular pumping efficiency. In delivering such therapy, for example, it may be useful to pace only one ventricle on an inhibited demand basis in accordance with sense signals received from the opposite ventricle, pace one ventricle in a triggered mode in which an intrinsic beat in one ventricle triggers a pace in the opposite ventricle, pace both ventricles on an inhibited demand basis in accordance with sense signals received from only one ventricle, or pace both ventricles in a combination of triggered and inhibited demand modes. In the examples of resynchronization therapy that follow, the ventricular pacing modes are based upon intrinsic activity in the right ventricle. It should be appreciated, however, that equivalent embodiments could be applied to pacing modes based upon left ventricular intrinsic activity.

One implementation of resynchronization therapy is biventricular (BV) pacing. In BV pacing, a left ventricular pace is delivered either simultaneously or in a timed relation with a right ventricle pace as specified by a biventricular offset interval. The offset interval may be zero in order to pace both ventricles simultaneously, positive in order to pace the left ventricle after the right, or negative if the left ventricle is paced before the right. In many cases, pumping efficiency of the heart will be increased by simultaneous pacing of the ventricles with an offset of zero. However, it may be desirable in certain patients to pace one ventricle before the other in order to compensate for different conduction velocities in the two ventricles, and this may be accomplished by specifying a particular biventricular offset interval. The ventricles may be paced on an inhibited demand basis where the ventricular escape interval is restarted with either a ventricular pace or a right ventricular sense. The pacing mode may also include atrial tracking. In that case, a pair of ventricular paces are delivered after expiration of the AVI escape interval or expiration of the LRL escape interval, with ventricular pacing inhibited by a right ventricular sense that restarts the LRL escape interval or stops the AVI escape interval. Since the ventricular escape interval in this mode is reset or stopped by senses only from the right ventricle, a left ventricular protection period may be provided that starts with the occurrence of a left ventricular sense and lasts for a specified time. A left ventricular pace is then not permitted upon expiration of the escape interval if it would occur within the protection period.

A variation of biventricular pacing is to pace only the left ventricle (LV-only pacing). LV-only pacing may be advantageous where the conduction velocities within the ventricles are such that pacing only the left ventricle results in a more coordinated contraction by the ventricles than with conventional right ventricular pacing or biventricular pacing. LV-only pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval or stops the AVI escape interval. As with BV pacing, a left ventricular pace may be inhibited if a left ventricular sense occurs within a protective period prior to expiration of the ventricular escape interval. Since an inhibited left ventricular pace in this mode could result in a cardiac cycle with no pacing, the mode may be further modified such that a right ventricular safety pace is delivered if the left ventricular pace is inhibited and no right ventricular sense has occurred.

Another ventricular resynchronization mode is a biventricular triggered (BT) mode where one or both ventricles are paced within a latency period following a sense from the right ventricle. In this mode, rather than inhibiting pacing upon receipt of a right ventricular sense, ventricular pacing is triggered to occur in the shortest time possible after a right ventricular sense in order produce a coordinated contraction of the ventricles. This mode of pacing may be desirable when the intraventricular conduction time of the heart is long enough that the pacemaker is able to reliably insert a pace before depolarization from the right ventricle would reach the left ventricle. The time delay between a right ventricular sense and the ensuing pace output is dictated by the response time of the hardware and is designated as the sense-to-pace latency (SPL) interval. Note that the SPL interval is a characteristic of the hardware and not a programmable timer interval. The mode may operate such that following a right ventricular sense, either the left ventricle only is paced, or both ventricles are paced. In the latter case, the right ventricle is paced even though a right ventricular sense has been received to allow for the possibility that the right ventricular sense was actually a far-field left ventricular sense in the right ventricular channel. If the right ventricular sense were actually from the right ventricle, the right ventricular pace would occur during the right ventricle's physiological refractory period and be of no consequence. With either type of BT pacing mode, pacing of the left ventricle can be inhibited by a left ventricular sense that triggers a left ventricular protective period interval. Biventricular triggered pacing can also be combined with biventricular inhibited demand pacing.

4. Ventricular Rate Regularization

Ventricular rate regularization (VRR) is a ventricular pacing mode in which the LRL of the pacemaker is dynamically adjusted in accordance with a detected intrinsic ventricular rate. When a pacemaker is operating in a ventricular pacing mode (e.g., VVI), intrinsic ventricular beats occur when the instantaneous intrinsic rate rises above the LRL of the pacemaker. Otherwise, paces are delivered at a rate equal to the LRL. Thus, paces are interspersed with intrinsic beats, and the overall ventricular rhythm as a result of both paces and intrinsic beats is determined by the LRL and the mean value and variability of the intrinsic ventricular rate. VRR regularizes the overall ventricular rhythm by adjusting the LRL of the pacemaker in accordance with changes in the measured intrinsic rate.

The intrinsic ventricular rate is the rate at which intrinsic ventricular beats occur and can be defined both instantaneously and as being at some mean value with a certain variability about that mean. The instantaneous intrinsic rate can be determined by measuring an R-R interval, where an R-R interval is the time between a present ventricular sense (i.e., an R-wave or intrinsic ventricular depolarization) and the preceding ventricular sense or ventricular pace, with the instantaneous rate being the reciprocal of the measured interval. The LRL of a pacemaker is initially set to a programmed base value and defines the ventricular escape interval, which is the maximum time between ventricular beats allowed by the pacemaker and is the reciprocal of the LRL. At any particular mean intrinsic rate above the LRL, a ventricular pace is delivered only when, due to the variability in the intrinsic rate, an R-R interval would be longer than the ventricular escape interval were it allowed to occur. As the mean intrinsic ventricular rate increases above the LRL, fewer paces are delivered and more variability in the overall ventricular rhythm is allowed. The VRR pacing mode counteracts this by increasing the LRL as the intrinsic ventricular rate increases to thereby increase the frequency of paced beats and lessen the variability in the overall ventricular rate. The VRR mode then decreases the LRL toward its base value as the number of paces delivered increases due to a decrease in either the mean intrinsic ventricular rate or its variability. The LRL adjusted in this manner is also referred to herein as the VRR-indicated rate.

Figure 2A:
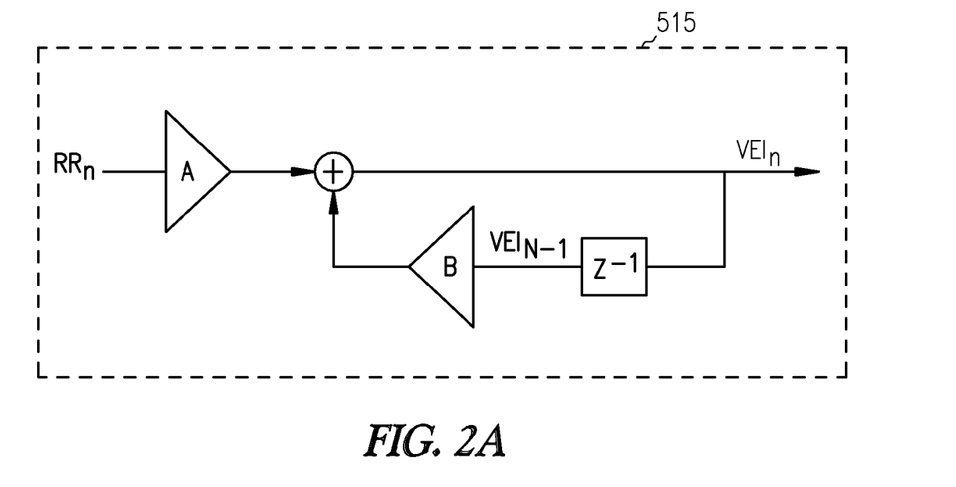
FIGS. 2A and 2B show an exemplary filter implementation of a ventricular rate regularization system.
Figure 2B:
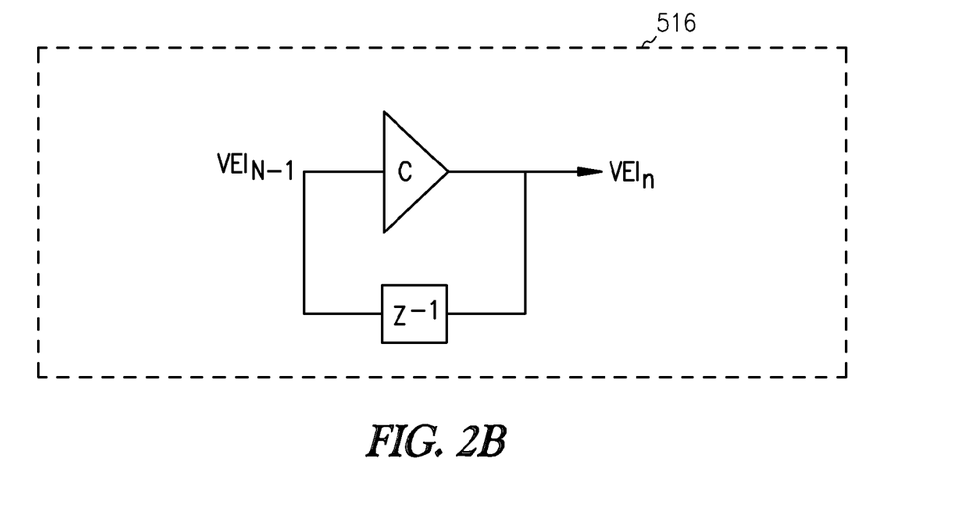

In one embodiment of VRR, the LRL is adjusted by measuring an R-R interval when a ventricular sense occurs and then computing an updated ventricular escape interval based upon the measured R-R interval. When a ventricular pace is delivered, on the other hand, the LRL is made to decay toward the programmed base value. FIGS. 2A and 2B show an exemplary implementation of a VRR system made up of a pair of filters 515 and 516 which may be implemented as software executed by the controller 10 and/or with discrete components. Filter 515 is employed to compute the updated ventricular escape interval when a ventricular sense occurs, and filter 516 is used when a ventricular pace is delivered.

When a ventricular sense occurs, the measured R-R interval is input to a recursive digital filter 515 whose output is the updated ventricular escape interval. The filter 515 multiplies the measured R-R interval by a filter coefficient A and then adds the result to the previous value of the output (i.e., the present ventricular escape interval) multiplied by a filter coefficient B. The operation of the filter is thus described by $VEI_n = A(RR_n) + B(VEI_{n-1})$, where A and B are selected coefficients, $RR_n$ is the most recent R-R interval duration, and $VEI_{n-1}$ is the previous value of the ventricular escape interval. A useful way to conceptualize the filter 515 is to decompose the coefficients A and B into a scaling factor a and a weighting coefficient w such that $A = a \cdot w$ and $B = (1-w)$, where w is between 0 and 1. Viewed this way, the filter is seen as computing a weighted average of the present R-R interval multiplied by the scaling factor a and the present ventricular escape interval. The filter thus causes the value of the ventricular escape interval to move toward the present R-R interval multiplied by the scaling factor at a rate determined by the weighting coefficient. This corresponds to the filter moving the pacemaker's LRL toward a fraction 1/a of the instantaneous intrinsic ventricular rate as determined by the measured R-R interval. If a ventricular sense has occurred, the current LRL is necessarily less than the measured instantaneous intrinsic ventricular rate. If it is also less than 1/a of the intrinsic rate, the LRL is increased by the filter up to a value that is 1/a of the intrinsic rate to result in more pacing and less variability in the overall ventricular rhythm.

When a ventricular pace is delivered due to expiration of the ventricular escape interval without a ventricular sense, filter 516 multiplies the present ventricular escape interval by a filter coefficient C so that $VEI_n = C(VEI_{n-1})$. To provide stable operation, the coefficient C must be set to a value greater than 1. Filter 516 then causes the ventricular escape interval to increase in an exponential manner with each pace as successive values of the escape interval are input to the filter up to a value corresponding to the base LRL.

The updating of the ventricular escape interval may be performed in various ways including on a beat-to-beat basis, at periodic intervals, or with averages of successive R-R intervals. In a presently preferred embodiment, however, the updating is performed on a beat-to-beat basis with each ventricular sense or pace causing adjustment of the LRL by filter 515 or 516, respectively. The two filters operating together thus cause the LRL to move closer to 1/a of the measured intrinsic rate after a ventricular sense and to decay toward the base LRL value after a ventricular pace.

The coefficients a and w (or A and B) and C are selected by the user and may be made programmable so that the behavior of the system can be adjusted to produce the clinically best result in an individual patient. For example, as the scaling factor a is made greater than 1, the filter 515 causes the LRL to move toward a smaller fraction 1/a of the detected intrinsic rate which allows more intrinsic beats to occur and greater variability in the overall rhythm. As a is decreased back toward 1, the filter 515 tends to move the LRL of the pacemaker toward a larger fraction of the detected instantaneous intrinsic rate, thus increasing the amount of pacing and decreasing the amount of variability allowed in the overall ventricular rhythm. If a is made smaller than 1, the LRL is moved toward a rate higher than the intrinsic rate, further increasing the amount of pacing to point where most of the ventricular rhythm is made up of paced beats. The larger the weighting factor w, the faster the LRL is moved to the specified fraction of the intrinsic rate, making the system more responsive to increases in the variability of the intrinsic rhythm. The larger the decay coefficient C, the more rapidly will filter 516 cause the LRL to decrease toward its programmed base value when ventricular paces are delivered due to no ventricular senses being detected within the ventricular escape interval. The controller limits the updated ventricular escape interval as a result of the operations of filters 515 and 516 to minimum and maximum values in accordance with a programmed maximum pacing rate MPR and base lower rate limit LRL, respectively.

As noted, the coefficients of filters 515 and 516 can be made programmable by the user, such as by using a remote programmer. In another embodiment, the user selects a desired performance parameter (e.g., desired degree of rate regularization, desired amount of pacing, desired decay rate, etc.) from a corresponding range of possible values. The appropriate combinations of coefficients for filters 515 and 516 are then automatically selected to provide filter settings that correspond to the selected user-programmed performance parameter. The filter coefficients can also be made functions of other parameters, such as the measured R-R interval and current LRL setting, and dynamically adjusted.

The VRR system in this embodiment uses the programmed base LRL of the pacemaker as the lower limit to which the LRL is permitted to decay when no ventricular senses are detected. The base LRL can be changed periodically by the user with an external programmer, and rate-adaptive pacemakers have the capability of dynamically adjusting the LRL in order to adapt to exercise. If a rate-adaptive pacemaker is operated in a VRR mode, the sensor-indicated rate can simply be regarded by the pacemaker as the base LRL. The lower limit for the VRR-indicated rate is then the sensor-indicated rate rather than the programmed base LRL.

5. Pacing Mode Switching During Atrial Fibrillation

Figure 3:
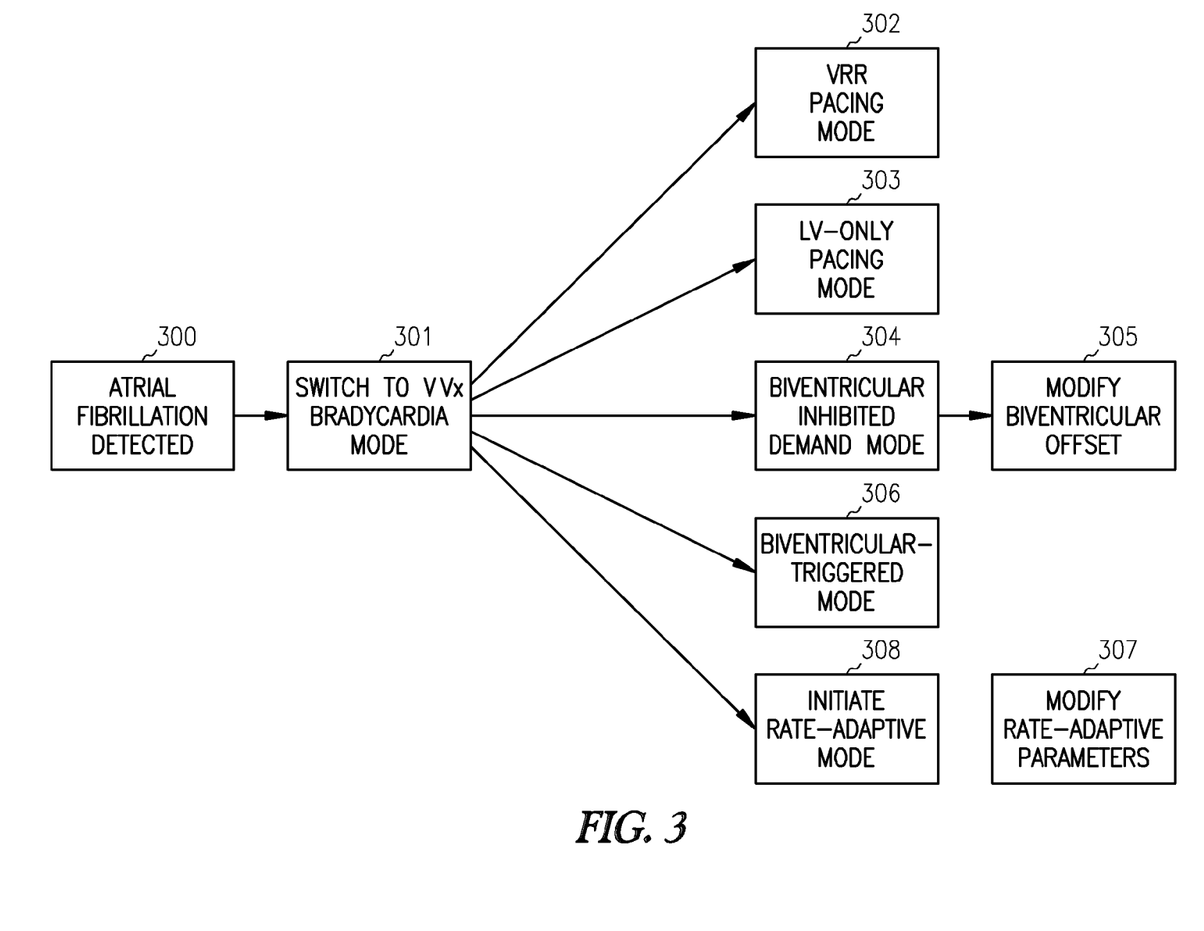
FIG. 3 is a block diagram illustrating exemplary atrial fibrillation pacing modes.

FIG. 3 is a block diagram illustrating examples of an atrial fibrillation pacing mode that is switched to upon detection of an atrial tachyarrhythmia. An atrial tachyarrhythmia, such as atrial fibrillation, is detected at block 300 while the pacemaker is operating in its normal mode. Atrial triggered ventricular pacing is contraindicated during an atrial tachyarrhythmia because atrial rate tracking would result in ventricular pacing that is too rapid. If the normal mode incorporates atrial tracking and/or atrial pacing, therefore, the atrial fibrillation mode includes a reversion to a non-atrial triggered ventricular pacing mode (i.e., VVx mode) as shown at block 301. The atrial fibrillation mode may also include one or more other pacing modes, each of which will be discussed in turn.

The atrial fibrillation mode may include initiation of ventricular rate regularization as shown at block 302. If AV conduction is intact in a patient, atrial fibrillation results in a very rapid and intrinsic ventricular rhythm, and regularizing the ventricular rate improves cardiac output directly through its effect on diastolic filling. Ventricular rate regularization may be applied in this instance with parameter settings such that the ventricles are driven at a rate near the intrinsic rate. The intrinsic ventricular rhythm that occurs during an episode of atrial fibrillation is a result of the chaotically occurring depolarizations occurring in the atria being passed through the AV node to the ventricles. The intrinsic ventricular rate is thus governed by the cycle length of the atrial fibrillation and the refractory period of the AV node. If a ventricular pacing pulse is delivered before the next intrinsic beat occurs, the ventricular depolarization is conducted retrogradely to the AV node causing late depolarization of the AV node during the ventricular beat. The refractory period of the AV node is also delayed, which delays the time before an atrial depolarization can be conducted through the node to result in an intrinsic beat. The effect of the pace is thus to lengthen the time until the next intrinsic beat. Ventricular rate regularization at a pacing rate near the intrinsic ventricular rate is thus especially effective at regularizing the ventricular rate during atrial fibrillation.

Ventricular resynchronization therapy may also be initiated as part of the atrial fibrillation mode. In pacemaker patients having some degree of interventricular or intraventricular conduction delays, a ventricular resynchronization pacing mode can improve cardiac output by improving the coordination of ventricular contractions. Although cardiac output may be adequate in some of these patients during normal circumstances even without ventricular resynchronization pacing, an episode of atrial fibrillation with loss of atrio-ventricular synchrony and irregular diastolic filling may cause the conduction deficits to become clinically evident. Switching the pacemaker to a ventricular resynchronization pacing mode may then be helpful in maintaining cardiac output when atrial fibrillation is detected.

Resynchronization pacing as incorporated into the atrial fibrillation mode may be delivered in a number of different pacing modes. One such resynchronization pacing mode is biventricular pacing with or without an offset interval. This mode can be combined with the reverted to VVI bradycardia pacing mode to result in biventricular pacing on an inhibited demand basis as depicted at block 304. Other alternatives for the atrial fibrillation mode are biventricular-triggered and LV-only pacing modes as shown by blocks 306 and 303, respectively. Biventricular-triggered resynchronization pacing may be particularly useful when the intrinsic ventricular rate is irregular as it allows reliable delivery of resynchronization pulses based upon the irregular rate. It may also be advantageous to combine resynchronization pacing with ventricular rate regulation as the ventricular rate regulation can be set to increase the amount of pacing and, therefore, the amount of resynchronization. If ventricular resynchronization is part of the normal pacing mode, the atrial fibrillation mode may then include particular modification of resynchronization pacing parameters such as adjustments to the biventricular offset interval designated by block 305, or switching to an alternative resynchronization pacing mode or switching to additional or alternate pacing sites.

The diminished cardiac output that occurs during atrial fibrillation can also be partially counteracted by making the pacing rate responsive to measured exertion levels. Accordingly, the atrial fibrillation mode may also include switching from non-rate adaptive to rate-adaptive pacing as shown at block 308, and/or modification of rate-adaptive parameters as shown at block 307. In the latter case, for example, the rate-response curve that maps a given exertion level to a particular pacing rate may be adjusted to make the pacemaker more responsive, and/or the base lower rate limit corresponding to a resting exertion level could be increased.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
sensing amplifiers for sensing atrial and ventricular depolarizations;
pulse generators for delivering paces to the right and left ventricles;
a controller for controlling the delivery of paces in accordance with a primary pacing mode that delivers paces to only one ventricle;
wherein the controller is configured to switch the pacemaker to an atrial fibrillation pacing mode upon detection of an atrial tachyarrhythmia, wherein the atrial fibrillation pacing mode includes a biventricular pacing mode that delivers paces to both left and right ventricles in a non-atrial triggered pacing mode in which the controller adjusts a ventricular escape interval in order to regularize the rate at which ventricular beats occur by increasing the ventricular escape interval after a ventricular pace is delivered and decreasing the ventricular escape interval after a ventricular sense.

2. The pacemaker of claim 1 wherein the adjustment of the ventricular escape interval is based on a previous value of the ventricular escape interval and a measured intrinsic ventricular rate.

3. The pacemaker of claim 1 wherein the adjustment of the ventricular escape interval is performed by increasing the ventricular escape interval after a ventricular pace is delivered and decreasing the ventricular escape interval after a ventricular sense by computing a weighted average of a previous value of the ventricular escape interval and an RR interval, where the RR interval is the interval between the ventricular sense and the preceding ventricular sense or pace.

4. The pacemaker of claim 1 wherein the adjustment of the ventricular escape interval is performed by increasing the ventricular escape interval after a ventricular pace is delivered by an amount depending upon a previous value of the ventricular escape interval.

5. The pacemaker of claim 1 wherein the adjustment of the ventricular escape interval is performed by increasing the ventricular escape interval after a ventricular pace is delivered by multiplying a previous value of the ventricular escape interval by a specified coefficient.

6. The pacemaker of claim 1 wherein the biventricular pacing mode delivers paces to both ventricles with a selected biventricular offset interval.

7. The pacemaker of claim 1 wherein the biventricular pacing mode is a biventricular triggered mode.

8. The pacemaker of claim 1 wherein the atrial fibrillation pacing mode includes adjustments to one or more rate-adaptive pacing parameters.

9. The pacemaker of claim 1 wherein the adjustment of the ventricular escape interval is performed on a beat-to-beat basis.

10. The pacemaker of claim 1 wherein the adjustment of the ventricular escape interval is performed periodically.

11. The pacemaker of claim 1 wherein the adjustment of the ventricular escape interval is performed based upon an average of successive R-R intervals.

12. The pacemaker of claim 1 wherein, in the atrial fibrillation pacing mode, the ventricular escape interval is increased after each ventricular pace is delivered and after each ventricular sense.

* * * * *